US00PP14008P29

(12) United States Plant Patent
Utecht

(10) Patent No.: US PP14,008 P2
(45) Date of Patent: Jul. 22, 2003

(54) GERANIUM PLANT NAMED 'FIP 101'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,592

(22) Filed: Sep. 30, 2002

(51) Int. Cl.[7] ..... A01H 5/00
(52) U.S. Cl. ..... Plt./332

(58) Field of Search ..... Plt./332

*Primary Examiner*—Kent Bell
(74) *Attorney, Agent, or Firm*—Foley & Lardner

(57) ABSTRACT

A new and distinct cultivar of geranium plant named 'Fip 101' characterized by the combined features of deep-red, double flowers, numerous small inflorescence, deep green, slightly zoned leaves, moderately short, well-branched, semi-trailing plant habit, early to medium spring flowering response, and generally healthy appearance without cultivation problems.

1 Drawing Sheet

Latin name of the genus and species of the plant claimed: *Pelargonium peltatum L'Héritier.*
Variety denomination: 'Fip 101'.

BACKGROUND OF THE INVENTION

The present invention comprises a new and distinct cultivar of geranium, botanically known as *Pelargonium peltatum,* and hereinafter referred to by the cultivar name 'Fip 101'.

'Fip 101' is a product of a planned breeding program which had the objective of creating new ivy geranium cultivars with red, double flowers, and moderately compact, but well-branched growth habit.

'Fip 101' originated from a hybridization made by the inventor Angelika Utecht in a controlled breeding program in Galdar, Gran Canaria, Spain, in 1997.

The female parent was the patented variety 'Fizzard' (U.S. Plant Pat. No. 10,992), characterized by large, single-type, deep red flowers, medium green foliage with weak zonation, and vigorous, long trailing growth habit. The male parent of 'Fip 101' was the unpatented hybrid seedling no. '93-361-3', having red, semi-double flowers, large foliage with weak zonation, and vigorous growth.

'Fip 101' was selected as one flowering plant within the progeny of the stated cross by Angelika Utecht in 1998 in a controlled environment in Galdar, Gran Canaria, Spain. The first act of asexual reproduction of 'Fip 101' was accomplished when vegetative cuttings were taken from the initial selection in the fall of 1998 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fip 101' are firmly fixed and are retained through successive generations of asexual reproduction.

'Fip 101' has not been observed under all possible environmental conditions. The phenotype may vary significantly with variations in environment such as temperature, light intensity and day length.

The following observations, measurements, and comparisons describe plants grown in Hillscheid, Germany under greenhouse conditions which approximate those generally used in commercial practice.

BRIEF SUMMARY OF THE INVENTION

The following traits have been repeatedly observed and are determined to be basic characteristics of 'Fip 101' in combination distinguish this geranium as a new and distinct cultivar:

1. Brilliant red, semi-double to double flowers;
2. Numerous, small, tight inflorescences;
3. Medium-green foliage, small leaves with weak zonation;
4. Compact to medium sized plant habit, bushy and well-branched;
5. Early to medium spring flowering response; and
6. Excellent heat tolerance, no development of white shoot tips.

Of the many commercial cultivars known to the present inventor, the most similar in comparison to 'Fip 101' are the patented varieties 'Fizzard', the parental variety, 'Fisbeach' (U.S. Plant Pat. No. 12,408), and 'Guishiva' (U.S. Plant Pat. No. 9,351).

In comparison to 'Fizzard', 'Fip 101' has a similar red flower color, but flowers are smaller in size and have semi-double to double form, in contrast to the single-type flowers of 'Fizzard'. Furthermore, the plant habit of 'Fip 101' is much more compact with shorter internodes.

In comparison to 'Fisbeach', 'Fip 101' has a similar flower color and shape, but smaller leaves with weak zonation, and distinctly more compact plant habit, while 'Fisbeach' has no zonation.

In comparison to 'Guishiva', 'Fip 101' has even smaller flowers, shorter peduncles, differently shaped leaves with less distinct zonation, and similar or somewhat smaller plant habit with the branches spreading more horizontally and less upright than those of 'Guishiva'.

BRIEF DESCRIPTION OF THE DRAWING

The accompanying photographic drawing shows typical flower and foliage characteristics of 'Fip 101' with colors being as true as possible with an illustration of this type. The drawing depicts a branch end of 'Fip 101' with typical leaves, buds and inflorescences.

DETAILED BOTANICAL DESCRIPTION

Measurements were taken in Hillscheid, Germany, in mid May 2002, about 15 weeks after planting of rooted cuttings. The plants were growing in 14 cm plastic pots, they had been pinched once.

In the following description color references are made to The Royal Horticultural Society Colour Chart. The color values were determined indoors from plants developed in a greenhouse, as described.

Inflorescence:
- *Type.*—Umbel, semi-spherically shaped.
- *Average diameter.*—75–85 mm.
- *Average depth.*—45 mm.
- *Peduncle length.*—100–120 mm.
- *Peduncle color.*—Light green, RHS 143 B.
- *Pedicel.*—18–20 mm long; spur present, but hardly visible, most often fused with the largest sepal.
- *Pedicel color.*—Bright green, RHS 143 A to 143 B, outdoor partly dark reddish-brown, RHS 183 A.
- *Number of flowers per umbel.*—About 11–16.

Corolla:
- *Average diameter.*—46 mm.
- *Form.*—Double-type.
- *Shape.*—Star-shaped, somewhat irregular, relatively narrow petals.
- *Number of petals.*—11–13.
- *Shape of petals.*—Spatulate or narrow-obovate, base acute, upper end is rounded, margin is entire or very weakly crenated.
- *Size of petals.*—Upper petals: 26–27 mm long, 13–15 mm wide. Lower petals: 24–26 mm long, 14–15 mm wide.
- *Color (general tonality from a distance of three meters)*.—Deep true red.
- *Color of upper petals.*—Main part RHS 46 B.
- *Markings of upper petals.*—Two blackish veins, RHS 187 A.
- *Color of lower petals.*—RHS 46 B.
- *Markings of lower petals.*—None.
- *Color of lower surface of petals.*—Dull light red, between RHS 46 C and RHS 53 C.
- *Color of sepals, main color.*—Outer surface: light green, RHS 143 B, inner surface: light green, RHS 143 C.
- *Color of upper sepal.*—Partly brownish, RHS 181 A, lower surface RHS 182.
- *Number of sepals.*—5.
- *Shape of sepals.*—Lanceolete, acute tip, truncate base, surface slightly glossy, with very weak pubescence, margin entire.
- *Size of sepals.*—15–16 mm long, 4–5 mm wide for the largest upper sepal, 2–3 mm in width for the other sepals.

Bud (just prior to petals unfolding):
- *Shape.*—Narrow elliptical.
- *Color of sepals.*—Light green, RHS 143 C.
- *Color of petals.*—RHS 46 B.
- *Length.*—18 mm.
- *Width.*—6–7 mm.

Reproductive organs:
- *Androecium.*—5–7 anthers, pale yellow, RHS 11 B, most often sterile, no pollen, white filaments, RHS 155 D.
- *Gynoecium.*—One pistil, pink style, RHS 51 B, 5–6-lobed stigma, dark-red, RHS 46 A.
- *Fertility/seed set.*—No seed set observed.

Spring flowering response period: In Hillscheid, Germany, in 2001 plants had on average 1.4 flowers open 12 weeks after planting of rooted cuttings.

Outdoor flower production: Continuously and rich flowering, the flower count in 2001 in Hillscheid, Germany, indicated about 6 inflorescence per plant in mid May.

Durability: Good stability of flower color, no fading, fair rain resistance.

Lastingness of the individual flower: About 7–8 days at 18° C.

Fragrance: None.

PLANT

Foliage:
- *Shape.*—Ivy-shaped, with cordate base, open to wide open gap between the lowest lobes, apex rounded, with distinct lobes.
- *Margin.*—Mostly entire, occasionally single, weak notches near the tips of lobes.
- *Texture.*—Leathery, upper surface smooth and glossy, healthy looking, no tendency to developing oedema under moist weather conditions, surface not quite flat, but often folded near tips of lobes.
- *Size of leaf.*—70–80 mm wide, 40–45 mm long.
- *Color of upper surface.*—Deep green, closest to RHS 137 B.
- *Zonation.*—Narrow ring shape, weak, brown, about RHS 166 A.
- *Color of lower surface.*—RHS 143 B.
- *Petioles.*—30–40 mm long, 2.5–3 mm diameter, light green in color, approximately RHS 143 B.

General appearance and form:
- *Stem color.*—Green, RHS 143 A.
- *Internode length.*—30–40 mm.
- *Branching pattern.*—9.6 branches.
- *Length of plants.*—22.5 cm (15 week-old plants, as described), 55.0 cm (28 week-old plants in mid August); measured from the top of the soil (base of the main stem) to the tips of the branches (measured without inflorescence).

Disease/pest resistance/susceptibility: No observations to date.

I claim:

1. A new and distinct cultivar of geranium plant named 'Fip 101', as described and illustrated herein.

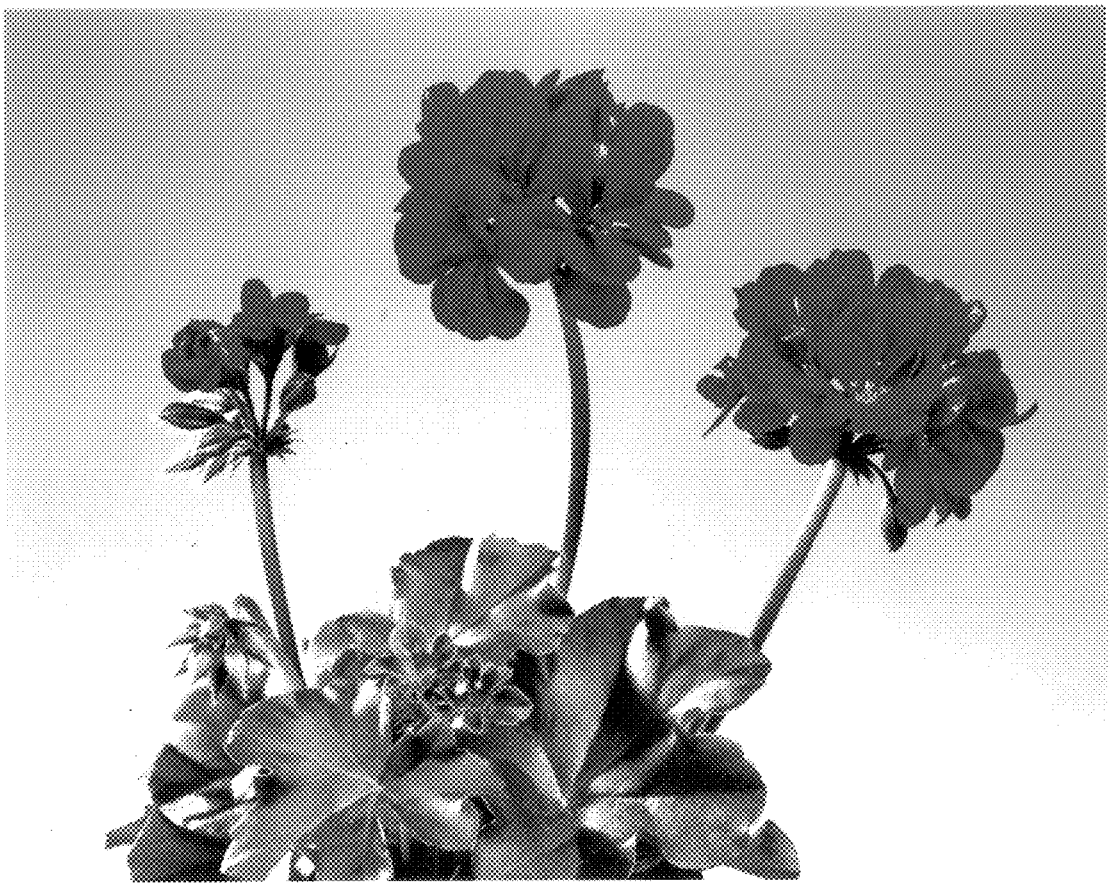

* * * * *